US006481154B1

(12) United States Patent
Nakamura et al.

(10) Patent No.: US 6,481,154 B1
(45) Date of Patent: Nov. 19, 2002

(54) METHOD OF LARGE-SCALE PROPAGATION OF TREES OF GENUS SWIETENIA

(75) Inventors: Kentaro Nakamura, Ibaraki (JP); Ryo Soda, Ibaraki (JP)

(73) Assignee: Sumitomo Forestry Co., Ltd., Osaka (JP)

( * ) Notice: Subject to any disclaimer, the term of this patent is extended or adjusted under 35 U.S.C. 154(b) by 0 days.

(21) Appl. No.: 09/508,819

(22) PCT Filed: Oct. 14, 1997

(86) PCT No.: PCT/JP97/03681

§ 371 (c)(1),
(2), (4) Date: Mar. 17, 2000

(87) PCT Pub. No.: WO99/18773

PCT Pub. Date: Apr. 22, 1999

(51) Int. Cl.[7] .............................. A01H 4/00; C12N 5/00
(52) U.S. Cl. ........................ 47/58.1; 435/410; 435/430; 435/41; 800/298; 800/295
(58) Field of Search ............................. 47/58; 800/298, 800/295; 435/41, 410, 430; A01H 4/00; C12N 5/00

(56) References Cited

U.S. PATENT DOCUMENTS

| | | | | |
|---|---|---|---|---|
| 4,152,869 A | * | 5/1979 | Jones | 47/58 |
| 4,338,745 A | * | 7/1982 | Misawa et al. | 47/58 |
| 4,353,184 A | * | 10/1982 | Abo El-Nil | 47/58 |
| 4,992,375 A | * | 2/1991 | Wright | 435/240.5 |
| 5,034,326 A | * | 7/1991 | Pullman et al. | 435/240.4 |
| 5,236,841 A | * | 8/1993 | Gupta et al. | 435/240.45 |
| 5,482,857 A | * | 1/1996 | Gupta et al. | 435/240.45 |
| 5,750,401 A | * | 5/1998 | Phadke et al. | 435/430 |

FOREIGN PATENT DOCUMENTS

| | | | | |
|---|---|---|---|---|
| JP | 405146232 A | * | 6/1993 | A01H/4/00 |
| JP | 06153731 A | | 6/1994 | |
| JP | 09019229 A | | 1/1997 | |
| JP | 09019229 A | * | 1/1997 | A01H/4/00 |
| JP | 09056286 A | | 3/1997 | |

OTHER PUBLICATIONS

EPO Search Report Reference No. 10675/CH/bm; Application No. 97944110.2–2313–JP9703681 with Abstract as attachment (Dec. 11, 2000).

S.K. Lee, et al., Gard. Bull. Sing. 41(1), 11–18 (1988).

S. Venketeswaran, et al. Cell Genetics of Woody Plants, 147–153 (1988).

Maruyama, et al. Tissue Culture of Eleven Tree species of Perü–Amazon Forest, 252–261 (1989).

Tissue Culture Studies on Mahogany Tree, Sweitenia, by S. Venketeswaran et al, Somatic Cell Genetics of Woody Plants, 147–153 (1988) Kluwer Academic Publishers.*

* cited by examiner

Primary Examiner—Peter M. Poon
Assistant Examiner—Andrea Valenti
(74) Attorney, Agent, or Firm—Connolly Bove Lodge & Hutz LLP

(57) ABSTRACT

Terminal buds or axillary buds of trees of genus Swietenia is cultured on a B5 medium containing 3-indole butyric acid (IBA) and benzylaminopurine (BAP) or its modified medium to induce multiple shoots; the multiple shoots are transplanted to a similar medium containing IBA and BAP to the above and cultured by liquid gyratory culture to efficiently propagate the multiple shoots; then the propagated multiple shoots are transplanted to a similar medium containing IBA and BAP to the above and subjected to liquid stationary culture to efficiently elongate a large number of the shoots; and the elongated shoots are transplanted to a similar medium containing IBA to the above to promote shoot elongation and rooting, thereby producing a large number of young plantlets of trees of genus Swietenia.

17 Claims, No Drawings

METHOD OF LARGE-SCALE PROPAGATION OF TREES OF GENUS SWIETENIA

TECHNICAL FIELD

The present invention relates to a method for large-scale propagation of trees of genus Swietenia, particularly *Swietenia macrophylla* KING belonging to the genus Swietenia by tissue culture.

BACKGROUND ART

Trees of genus Swietenia are major afforested trees in tropical zones of the world, and their loss due to pest injuries is a serious problem. Recent progress of tissue culture technique has enabled new species having resistances to diseases and pests in many plants, and provision of trees of genus Swietenia with a resistance to pests is expectable. Generally, conventional techniques such as afforestation based on cuttings, etc. are not acceptable in attempts to propagate useful old trees. It is also understood that propagation of elite tree and/or plus trees is hard to conduct.

Recently, several research groups have been studying tissue culture techniques to solve the problems so far encountered. In this connection, only four successful results have been reported up to now (S. Venketeswaran, M. A. D. L. Dias, F. Sultranbawa, U. V. Weyers (1988): Tissue culture on mahogany tree, Swietenia, Somatic Cell Genetics of Woody Plants: 147–153; S. K. Lee, A. N. Rao (1988): Plantlet production of *Swietenia macrophylla* king through tissue culture, Gard. Bull. Sing. 41(1): 11–18; E. Maruyama, K. Ishii, A. Saito, K. Migita (1989): Screening of suitable sterilization of explants and proper media for tissue culture of eleven tree species of Peru-Amazon forest, Journal of Agricultural Science 33(4): 252–261; and T. Kondo, M. Okamura (1994): Tissue culture of culturing of Woody Plants (Special Issue) '94: 4–5). However these studies are limited to shoot regeneration and induction of multiple shoots even when young plantlets germinated under aseptic conditions or terminal buds are used as materials, and regeneration of plantlets is not realized and regeneration and large-scale propagation of young plantlets from mature trees cannot be attained. Thus, development of an efficient culturing method has been keenly desired.

DISCLOSURE OF THE INVENTION

An object of the present invention is to provide a large-scale propagation method, which enables large-scale production of trees of genus Swietenia, particularly *Swietenia macrophylla* KING.

As a result of extensive studies on development of a large-scale propagation method enabling a large-scale production of nursery stocks or mature trees of genus Swietenia, the present inventors succeeded in induction of multiple shoots having definite buds and/or adventitious buds by culturing terminal buds or axillary buds of trees of genus Swietenia and furthermore in efficient propagation of the induced multiple shoots. It was further found that efficient induction and propagation of multiple shoots could be attained particularly by adding 3-indole butyric acid (IBA) and benzylaminopurine (BAP) to an induction medium for inducing multiple shoots and a medium for propagating the multiple shoots, and furthermore that the propagation efficiency of multiple shoots could be increased by liquid gyratory culture for propagating the multiple shoots. It was also found that efficient shoot elongation could be promoted by adding IBA and BAP to the medium and by liquid stationary culture in the elongation of shoots from the multiple shoots. Still furthermore, it was found that further shoot elongation and rooting could be attained by culturing the propagated shoots on a medium containing IBA.

The process for the large-scale propagation of trees of genus Swietenia according to the present invention, which comprises the steps of:

culturing terminal buds or axillary buds of trees of genus Swietenia on a multiple shoots-inducing medium, thereby inducing multiple shoots having a large number of definite buds and/or adventitious buds;

transplanting the resulting multiple shoots to a propagation medium and propagating the transplanted multiple shoots;

transplanting the propagated multiple shoots to a shoot elongation medium and subjecting the transplanted, propagated multiple shoots by stationary culture, thereby promoting shoot elongation; and transplanting the elongated shoots to a rooting medium, thereby rooting the transplanted elongated shoots to regenerate the plantlets of trees of genus Swietenia.

BEST MODES FOR CARRYING OUT THE INVENTION

According to the present invention, a large number of young plantlets of trees of genus Swietenia can be efficiently produced by inducing and propagating multiple shoots from terminal buds or axillary buds of nursery stocks and mature trees, then elongating shoots from the multiple shoots so obtained and rooting the elongated shoots.

Trees of genus Swietenia for use in the present invention includes, for example, *Swietenia macrophylla* KING.

Culture materials for use in the present invention include, for example, terminal buds or axillary buds excised from nursery stocks and mature trees. The excised terminal buds or axillary buds are subjected to surface sterilization with ethanol and sodium hypochlorite or aqueous hydrogen peroxide solution or mercuric chloride (corrosive sublimate) according to the ordinary procedure, and washed with sterilized water an then cultured on a medium.

The multiple shoots-inducing medium for use in the induction of multiple shoots from terminal buds or axillary buds is an ordinary basal medium containing an inorganic component and a carbon source as essential components, and also containing a plant growth regulator, a vitamin and amino acid. The inorganic component includes inorganic compounds containing such elements as nitrogen, phosphorus, potassium, sodium, calcium, sulfur, iron, manganese, zinc, boron, molybdenum, chlorine, cobalt, etc. The carbon source includes carbohydrates such as sucrose and glucose. The plant growth regulator includes, for example, auxin and cytokinin. The auxin includes, for example, 3-indole butyric acid (IBA), naphthalene acetic acid (NAA), etc. The cytokinin includes, for example, benzylaminopurine (BAP), kinetin, zeatin, 1-phenyl-3-(1,2, 3-Thiadiazol-5-YL)-Urea (Thidiazuron), etc. The vitamin includes, for example, thiamine, pyridoxine, nicotinic acid, etc. The amino acid includes, for example, glycine, glutamic acid, lysine, etc.

The medium for use in the actual culture is a medium used for plant tissue culture, such as a MS medium (Murashige, T. (1962), Physiol Plant 15: 473–497), a B5 medium (Gramborg, O. L. (1968), Exp. Cell Res. 50: 151–158), a WP medium (Lloyd, G. (1981), Int. Plant prop. Soc. 30: 421–427), an BTM medium (Chalupa, V. (1984) Biologia Plnt. 26: 374–377), etc. Or, their modified media such as a modified MS medium, a modified B5 medium, a modified WP medium, a modified BTM medium, etc. may be used, where the modified media designate media containing each of components in the basic media such as MS, B5, WP and BTM media at a changed concentration of, for example, half or one-fourth of the concentration in the basic media.

Particularly preferable are a B5 medium and its modified medium. To promote induction and growth of definite buds and adventitious buds, it is preferable to use a medium containing 0.02 to 1.0 mg/l of BAP or not more than 0.02 mg/l of IBA together with 0.02 to 1.0 mg/l of BAP.

Then, the multiple shoots so obtained are transplanted to a propagation medium to efficiently propagate the transplanted multiple shoots.

As a propagation medium, the above-mentioned basal medium can be used. Particularly, a medium containing an inorganic component, a carbon source, a vitamin, amino acid, etc. and also containing 0.02 to 0.2 mg/l of IBA and 0.2 to 2.0 mg/l of BAP is preferable. In actual culture, it is preferable to use a B5 medium containing such amounts of IBA and BAP as above or its modified medium. A solid or liquid medium is preferably used for the culture, and particularly a liquid gyratory culture is preferably used. More specifically a liquid gyratory culture under a gyratory condition of 60 to 100 rpm, preferably 70 to 80 rpm, is preferable.

Then, the propagated multiple shoots are translated to a shoot elongation medium to efficiently elongate shoots from the transplanted multiple shoots.

As a shoot elongation medium, the abovementioned basal medium can be used. Particularly, a medium containing an inorganic component, a carbon source, a vitamin, amino acid, etc. and also containing 0.02 to 0.2 mg/l of IBA and 0.2 to 2.0 mg/l of BAP is preferable. More specifically, a B5 medium containing such amounts of IBA and BAP as above or its modified medium is preferably used. A solid or liquid medium is preferably used for the culture, and particularly a liquid stationary culture is preferable.

Then, the elongated shoots are transplanted to a rooting medium with or without cutting to single shoots to further elongate and root the shoots.

As a rooting medium, the above-mentioned basal medium can be used, and particularly a medium containing an inorganic component, a carbon source, a vitamin, amino acid, etc. and also containing 1.0 to 5.0 mg/l of IBA is preferable. Actually, a B5 medium containing such an amount of IBA as above or its modified medium is preferable.

According to the present invention it is preferable to culture elongated shoots on a modified MS medium containing 1.0 to 3.0 mg/l of IBA, and transplant and culture the further elongated shoots to and on a modified B5 medium containing 1.0 to 3.0 mg/l of IBA, thereby rooting the shoots and regenerating the plantlets. The modified MS medium and modified B5 medium to be used each preferably contain 2.5 mg/l of IBA. Culturing time on the modified MS medium and modified B5 medium depends on culturing conditions, and usually is 15 days to one month, and particularly preferably about one month. Preferable culturing conditions are a temperature of 23° to 30° C., a humidity of 60 to 100%, and a light intensity of 3,000 to 9,000 Lux.

According to the present invention, it is preferable, after culturing on the above-mentioned modified MS medium and modified B5 medium to culture the shoots on a modified MS medium containing 1.0 to 3.0 mg/l or IBA for 15 days to one month, preferably for about one month. It is particularly preferable to use a modified MS medium containing 2.5 mg/l of IBA. Culturing conditions on the modified MS medium are the same as above.

By culturing in the above-mentioned specific modified medium, the shoot rooting rate can be elevated, whereas the withering rate can be lowered.

According to one of preferable modes for carrying out the present method for the large-scale propagation of trees of genus Swietenia by tissue culture, terminal buds or axillary buds of trees of genus Swietenia is at first cultured on a B5 medium containing BAP or IBA together with BAP or its modified medium to induce multiple shoots therefrom; then the multiple shoots are transplanted to a propagation medium containing IBA and BAP and cultured by a liquid gyratory culture to propagate the multiple shoots; then the propagated multiple shoots are transplanted to a shoot elongation medium containing IBA and BAP and cultured by liquid stationary culture, thereby promoting to elongate the shoots; and then the elongated shoots are transplanted to a rooting medium containing IBA and cultured, thereby producing young plantlets of trees of genus Swietenia.

EXAMPLE

The present invention will be described in detail below, referring to Example.

Nursery stocks of *Swietenia macrophylla* obtained from Indonesia (0.2 to 2.0 m high) were made to grow in a greenhouse to heights of 1.0 to 6.0 m, and then materials were excised therefrom.

(1) Sterilization of Materials

Terminal buds were excised from mature trees of *Swietenia macrophylla* and subjected to surface sterilization in 70% ethanol for 30 seconds and then in 2% sodium hypochlorite for 6 minutes, washed several times with sterilized water and dried on a sterilized filter paper.

(2) Induction of Multiple Shoots

To a modified B5 medium (which was a B5 medium amounts of all the components were each made a half were added 30 g/l of sucrose, and 0 to 0.02 mg/l of IBA and 0.02 to 1.0 mg/l of BAP as plant growth regulators, followed by pH adjustment to 5.7 and sterilization. The medium so prepared was used as a multiple shoots-inducing medium, and was used at a culturing temperature of 26±2° C. under illumination of fluorescent lamps for 16 hours per day (3,000 to 9,000 Lux). One to 3 months after the start of culturing, multiple shoots were induced.

Relations between the amounts of IBA and BAP added shoots the medium and number of formed multiple shoots are shown in Table 1.

TABLE 1

Conditions for inducing multiple shoots

| Plant growth regulator | | Number of formed multiple shoots/Number of total tested terminal buds |
|---|---|---|
| IBA (mg/l) | BAP (mg/l) | |
| 0 | 0.02 | 1/20 |
| 0 | 0.2 | 5/20 |
| 0 | 1.0 | 8/20 |
| 0.02 | 0.02 | 0/20 |
| 0.02 | 0.2 | 7/20 |
| 0.02 | 1.0 | 15/20 |

As is evident from the results shown in Table 1, addition of 0.02 mg/l of IBA and 1.0 mg/l of BAP is particularly effective.

(3) Propagation of Multiple Shoots

Multiple shoots obtained in (2) were cut to single shoots, which were transplanted to a propagation medium. A modified B5 medium (which was the same as used in (2)) containing 0.02 to 0.2 mg/l of IBA and 0.2 to 2.0 mg/l of BAP was used as a propagation medium after pH adjustment to 5.7 and sterilization. Culturing temperature was 26±2° C. under illumination of fluorescent lamps for 16 hours per day (3.00 to 9.000 Lux). As a result, about 6-fold shoots could be obtained 1 to 2 months after the start of culturing.

Relations between the amounts of IBA and BAP added to the medium and number of propagated shoots are shown in Table 2.

TABLE 2

Conditions for propagating multiple shoots

| Plant growth regulator | | Average number of propagated shoots/ |
|---|---|---|
| IBA | BAP | Multiple shoot |
| 0.02 | 0.2 | 4.1 |
| 0.02 | 0.5 | 4.7 |
| 0.02 | 2.0 | 1.2 |
| 0.2 | 0.2 | 5.9 |
| 0.2 | 0.5 | 3.1 |
| 0.2 | 2.0 | 0.7 |

As is evident from the results shown in Table 2, addition of 0.2 mg/l of IBA and 0.2 mg/l of BAP is particularly effective.

(4) Shoot Elongation

Multiple shoots propagated in (3) were transplanted as such to a shoot elongation medium. A modified B5 medium (which was the same as used in (2)) containing 0.02 mg/l of IBA and 0.2 to 2.0 mg/l of BAP was used as a shoot elongation medium after pH adjustment to 5.7 and sterilization. Culturing temperature was 26±2° C. under illumination of fluorescent lamps for 16 hours per day (3,000 to 9,000 Lux). As a result, all the shoots could be elongated to lengths of 5 to 10 mm one month after the start of culturing, and addition of 0.2 mg/l of IBA and 0.2 mg/l of BAP is particularly effective.

(5) Rooting

A large number of shoots obtained in (4) are cut to single shoots, which were then transplanted to a rooting medium. A modified B5 medium (which was the same as in (2)) containing 1.0 to 5.0 mg/l of IBA and 2.8 g/l of gerlite was used as a rotting medium after pH adjustment to 5.7 and sterilization. Culturing temperature was 26±2° C. under illumination of fluorescent lamps for 16 hours per day (3,000 to 9,000 Lux). It was observed that 18.5% of the single shoots were rooted one to two months after the start of culturing with shoot elongation of 3 to 5 cm and formation of 2 to 5 leaves.

Relations between the amount of IBA added to the medium and number of rooted single shoots are shown in Table 3.

TABLE 3

Rooting conditions

| Plant growth regulator IBA (mg/l) | Number of rooted single shoots |
|---|---|
| 1.0 | 1/27 |
| 2.0 | 2/30 |
| 2.5 | 5/27 |
| 3.0 | 0/26 |
| 4.0 | 1/25 |
| 5.0 | 0/26 |
| 10.0 | 0/26 |

As is evident from Tale 3, addition of 2.5 mg/l of IBA is effective.

(6) Rooting

A large number of shoots obtained in (4) were cut to single shoots which were cultured in the following procedures:

① The single shoots were cultured on a modified B5 medium containing 0 to 10.0 mg/l of IBA for 3 months, while transplanting the shoots to a fresh medium of the same composition every month.

② The single shoots were cultured on a modified MS medium containing 0 to 10.0 mg/l of IBA for 3 months, while transplanting the shoots to a fresh medium of the same composition every month.

③ The single shoots were cultured on a modified MS medium containing 0 to 10.0 mg/l of IBA for one month, then on a modified B5 medium containing 0 to 10.0 mg/l of IBA for one month and further on a modified MS medium containing 0 to 10.0 mg/l of IBA for one month.

④ The single shoots were cultured on a modified B5 medium containing 0 to 10.0 mg/l of IBA for one month, then on a modified MS medium containing 0 to 10.0 mg/l of IBA for one month and further on a modified B5 medium containing 0 to 10.0 mg/l of IBA for one month.

All the above ①–④ cultures were conducted under conditions wherein a temperature was 26±2° C., a humidity was 60 to 90% and a light intensity was 3,000 to 9,000 Lux. Further, all the modified media in the above ①–④ contained 2.8 g/l of gelright.

Results of culturing under the conditions of ① to ④ (rooting rate and withering rate) are shown in Tables 4 to 7.

TABLE 4

Rooting condition ①

| Medium | | | | Rooting rate (%) | | | Withering rate (%) | | |
|---|---|---|---|---|---|---|---|---|---|
| For first one month | For second one month | For third one month | IBA (mg/l) | For first one month | For second one month | For third one month | For first one month | For second one month | For third one month |
| Modified B5 | Modified B5 | Modified B5 | 0 | 0.0% | 0.0% | 0.0% | 92.3% | 100.0% | 100.0% |
| | | | 0.1 | 0.0% | 0.0% | 0.0% | 84.6% | 100.0% | 100.0% |
| | | | 1.0 | 0.0% | 3.7% | 3.7% | 14.8% | 55.6% | 96.3% |
| | | | 2.0 | 0.0% | 6.7% | 6.7% | 13.3% | 40.0% | 73.3% |
| | | | 2.5 | 0.0% | 18.5% | 18.5% | 11.1% | 40.7% | 66.7% |
| | | | 3.0 | 0.0% | 0.0% | 0.0% | 26.9% | 57.7% | 73.1% |
| | | | 4.0 | 0.0% | 4.0% | 4.0% | 40.0% | 72.0% | 100.0% |
| | | | 5.0 | 0.0% | 0.0% | 0.0% | 53.8% | 84.6% | 100.0% |
| | | | 10.0 | 0.0% | 0.0% | 0.0% | 80.8% | 96.2% | 100.0% |

TABLE 5

Rooting conditions ②

| Medium | | | | Rooting rate (%) | | | Withering rate (%) | | |
|---|---|---|---|---|---|---|---|---|---|
| For first one month | For second one month | For third one month | IBA (mg/l) | For first one month | For second one month | For third one month | For first one month | For second one month | For third one month |
| Modified MS | Modified MS | Modified MS | 0 | 0.0% | 0.0% | 0.0% | 19.2% | 84.6% | 92.3% |
| | | | 0.1 | 0.0% | 0.0% | 0.0% | 0.0% | 69.2% | 84.6% |
| | | | 1.0 | 0.0% | 3.8% | 3.8% | 0.0% | 46.2% | 73.1% |
| | | | 2.0 | 0.0% | 3.8% | 11.5% | 0.0% | 30.8% | 76.9% |
| | | | 2.5 | 0.0% | 13.3% | 16.7% | 0.0% | 26.7% | 66.7% |
| | | | 3.0 | 0.0% | 3.7% | 11.1% | 0.0% | 55.6% | 70.4% |
| | | | 4.0 | 0.0% | 0.0% | 0.0% | 10.3% | 58.6% | 96.6% |
| | | | 5.0 | 0.0% | 0.0% | 0.0% | 46.2% | 76.9% | 100.0% |
| | | | 10.0 | 0.0% | 0.0% | 0.0% | 65.4% | 80.8% | 100.0% |

TABLE 6

Rooting conditions ③

| Medium | | | | Rooting rate (%) | | | Withering rate (%) | | |
|---|---|---|---|---|---|---|---|---|---|
| For first one month | For second one month | For third one month | IBA (mg/l) | For first one month | For second one month | For third one month | For first one month | For second one month | For third one month |
| Modified MS | Modified MS | Modified MS | 0 | 0.0% | 0.0% | 0.0% | 26.9% | 69.2% | 76.9% |
| | | | 0.1 | 0.0% | 0.0% | 0.0% | 7.7% | 73.1% | 84.6% |
| | | | 1.0 | 0.0% | 10.0% | 40.0% | 0.0% | 30.0% | 50.0% |
| | | | 2.0 | 0.0% | 10.0% | 40.0% | 0.0% | 30.0% | 40.0% |
| | | | 2.5 | 0.0% | 40.0% | 70.0% | 0.0% | 0.0% | 20.0% |
| | | | 3.0 | 0.0% | 10.0% | 30.0% | 0.0% | 50.0% | 50.0% |
| | | | 4.0 | 0.0% | 0.0% | 0.0% | 20.0% | 60.0% | 80.0% |
| | | | 5.0 | 0.0% | 0.0% | 0.0% | 40.0% | 50.0% | 100.0% |
| | | | 10.0 | 0.0% | 0.0% | 0.0% | 50.0% | 100.0% | 100.0% |

TABLE 7

Rooting conditions (4)

| Medium | | | | Rooting rate (%) | | | Withering rate (%) | | |
| --- | --- | --- | --- | --- | --- | --- | --- | --- | --- |
| For first one month | For second one month | For third one month | IBA (mg/l) | For first one month | For second one month | For third one month | For first one month | For second one month | For third one month |
| Modified MS | Modified MS | Modified MS | 0 | 0.0% | 0.0% | 0.0% | 84.6% | 92.3% | 100.0% |
| | | | 0.1 | 0.0% | 0.0% | 0.0% | 84.6% | 88.5% | 100.0% |
| | | | 1.0 | 0.0% | 0.0% | 10.0% | 10.0% | 50.0% | 70.0% |
| | | | 2.0 | 0.0% | 10.0% | 10.0% | 0.0% | 40.0% | 50.0% |
| | | | 2.5 | 0.0% | 30.0% | 50.0% | 0.0% | 40.0% | 40.0% |
| | | | 3.0 | 0.0% | 10.0% | 20.0% | 0.0% | 60.0% | 70.0% |
| | | | 4.0 | 0.0% | 0.0% | 0.0% | 40.0% | 70.0% | 100.0% |
| | | | 5.0 | 0.0% | 0.0% | 0.0% | 50.0% | 90.0% | 100.0% |
| | | | 10.0 | 0.0% | 0.0% | 0.0% | 70.0% | 100.0% | 100.0% |

As is evident from the results shown in Tables 4 to 7, it was observed that in case of culturing according the procedure ③, 70.0% of the single shoots were rooted 3 months after the start of culturing with shoot elongation of 3 to 10 cm and formation of 2 to 5 new leaves, and addition of 2.5 mg/l of IBA is particularly effective.

That is, it was found more effective to culture the shoots on a modified MS medium containing 2.5 mg/l of IBA for one month, then on a modified B5 medium containing 2.5 mg/l of IBA for one month and further on a modified MS medium containing 2.5 mg/l of IBA for one month than to continuously culture them on a single kind of medium.

INDUSTRIAL UTILITY

According to the present invention, a large number of aseptic young plantlets for tissue culture of trees of genus Swietenia and nursery stocks and cuttings for cuttage can be produced in vitro for a short time with a high possibility of large-scale production of nursery stocks of trees of genus Swietenia.

What is claimed is:

1. A method for large-scale production of trees of genus Swietenia, which comprises the steps of:
    culturing terminal buds or axillary buds of trees of genus Swietenia on a multiple shoots-inducing medium wherein a B5 medium containing 0.02 to 1.0 mg/l of benzylaminopurine (BAP), or a B5 medium containing; not more than 0.02 mg/l of 3-indole butyric acid (IBA) together with 0.02 to 1.0 mg/l of BAP, or its modified B5 medium is used as the multiple shoots-inducing medium for inducting multiple shoots, thereby inducing multiple shoots having a large number of definite buds and/or adventions buds;
    transplanting the multiple shoots to a propagation medium, thereby propagating the multiple shoots;
    transplanting the propagated multiple shoots to a shoot elongation medium and subjecting the shoots to stationary culture, wherein the elongate shoots are cultured on a modified MS medium containing 1.0 to 3.0 mg/l of IBA, thereby promoting shoot elongation; and
    transplanting the elongated shoots to a modified B5 medium containing 1.0 to 3.0 mg/l of IBA and cultured, and rooting the shoots, thereby regenerating plantlets of trees of genus Swietenia.

2. A method according to claim 1, wherein the multiple shoots are propagated on the propagation medium by liquid gyratory culture, thereby increasing a propagation rate of multiple shoots.

3. A method according to claim 2, wherein a B5 medium containing 0.02 to 0.2 mg/l of IBA and 0.2 to 2.0 mg/l of BAP or its modified medium is used as the propagation medium.

4. A method according to claim 1, wherein a B5 medium containing 0.02 to 0.2 mg/l of IBA and 0.2 to 2.0 mg/l of BAP or its modified medium is used as the propagation medium.

5. A method according to claim 1, wherein the shoot elongation of the multiple shoots on the shoot elongation medium is carried out by liquid stationary culture.

6. A method according to claim 1, wherein a B5 medium containing 0.02 to 0.2 mg/l of IBA and 0.2 to 2.0 mg/l of BAP or its modified medium is used as the shoot elongation medium.

7. A method according to claim 1, wherein a B5 medium containing 1.0 to 5.0 mg/l of IBA or its modified medium is used a the rotting medium.

8. A method according to claim 1, wherein the trees of genus Swietenia is *Swietenia macrophylla* King.

9. A method according to claim 1, wherein a modified MS medium containing 2.5 mg/l of IBA and a modified B5 medium containing 2.5 mg/l of IBA are used as the modified MS medium and the modified B5 medium, respectively.

10. A method according to claim 9, wherein culture is carried out on the modified MS medium for about one month and then on the modified B5 medium for about one month.

11. A method according to claim 9, wherein culturing is further carried out on a modified MS medium containing 1.0 to 3.0 mg/l of IBA.

12. A method according to claim 1, wherein culture is carried out on the modified MS medium for about one month and then on the modified B5 medium for about one month.

13. A method according to any one of claim 1, wherein culturing is further carried out on a modified MS medium containing 1.0 to 3.0 mg/i of IBA.

14. A method according to claim 13, wherein a modified MS medium containing 2.5 mg/l of IBA is used as the modified MS medium.

15. A method according to claim 14, wherein culturing is carried out on the modified MS medium for about one month.

16. A method according to claim 13, wherein culturing is carried out on the modified MS medium for about one month.

17. A method according to claim 1, wherein B5 medium containing 0.02 to 0.2 mg/l of IBA and 0.2 to 2.0 mg/l of BAP or its modified medium is used as the propagation medium.

* * * * *